United States Patent
Kennedy et al.

(10) Patent No.: US 12,253,351 B2
(45) Date of Patent: Mar. 18, 2025

(54) OPTICAL PALPATION DEVICE AND METHOD FOR EVALUATING A MECHANICAL PROPERTY OF A SAMPLE MATERIAL

(71) Applicant: OncoRes Medical Pty Ltd, Nedlands (AU)

(72) Inventors: Brendan Francis Kennedy, Walliston (AU); Qi Fang, Claremont (AU); Rowan William Sanderson, Subiaco (AU)

(73) Assignee: OncoRes Medical Pty Ltd, Nedlands (AU)

( * ) Notice: Subject to any disclaimer, the term of this patent is extended or adjusted under 35 U.S.C. 154(b) by 691 days.

(21) Appl. No.: 17/286,555

(22) PCT Filed: Oct. 24, 2019

(86) PCT No.: PCT/AU2019/051171
§ 371 (c)(1),
(2) Date: Apr. 19, 2021

(87) PCT Pub. No.: WO2020/082133
PCT Pub. Date: Apr. 30, 2020

(65) Prior Publication Data
US 2021/0381823 A1    Dec. 9, 2021

(30) Foreign Application Priority Data
Oct. 24, 2018    (AU) .............................. 2018904043

(51) Int. Cl.
*G01B 11/16*    (2006.01)
*A61B 3/16*    (2006.01)
(Continued)

(52) U.S. Cl.
CPC ............ *G01B 11/16* (2013.01); *A61B 3/16* (2013.01); *A61B 5/0053* (2013.01);
(Continued)

(58) Field of Classification Search
CPC ..... A61B 5/0053; A61B 5/0082; G01B 11/16; G01L 1/24; G06T 7/593
See application file for complete search history.

(56) References Cited

U.S. PATENT DOCUMENTS 5,426,504 A    6/1995    Callender
8,144,271 B2    3/2012    Han
(Continued)

FOREIGN PATENT DOCUMENTS

CN    101566465 A    10/2009
JP    2005173575 A    6/2005
(Continued)

OTHER PUBLICATIONS

Japanese Patent Office Notification of Reason for Rejection for application No. 2021-547600, dated Jun. 16, 2023 (11 pages with translation).
(Continued)

*Primary Examiner* — Maurice C Smith
(74) *Attorney, Agent, or Firm* — Michael Best & Friedrich LLP

(57) ABSTRACT

The present disclosure provides an optical palpation device for evaluating a mechanical property of a sample material. The device comprises a body having a sensing portion and a sensing layer positioned at the sensing portion of the body and having a sensing surface positioned for direct or indirect contact with a surface area of the sample material. The sensing layer is deformable and has a predetermined deformation-dependent optical property. The device further comprises a light detector positioned to detect light transmitted (Continued)

through at least a portion of the sensing layer. The optical palpation device is arranged such that, when the sensing surface of the sensing layer is in direct or indirect contact with the surface area of the sample material and a pressure is applied through both the sensing layer and at least a portion of the surface area of the sample material, because of the predetermined deformation or pressure-dependent optical property of the sensing layer the mechanical property of the sample material is measurable by detecting the light that transmitted through at least a portion of the sensing layer.

20 Claims, 11 Drawing Sheets

(51) Int. Cl.
    *A61B 5/00*    (2006.01)
    *A61B 34/30*   (2016.01)
    *G01L 1/24*    (2006.01)
    *G01N 3/08*    (2006.01)

(52) U.S. Cl.
    CPC .......... *A61B 5/6806* (2013.01); *A61B 5/6848* (2013.01); *A61B 5/6853* (2013.01); *A61B 34/30* (2016.02); *G01B 11/165* (2013.01); *G01L 1/24* (2013.01); *G01N 3/08* (2013.01); *A61B 2034/301* (2016.02); *A61B 2562/0266* (2013.01); *G01N 2203/0019* (2013.01); *G01N 2203/0641* (2013.01)

(56) References Cited

U.S. PATENT DOCUMENTS

| | | | | |
|---|---|---|---|---|
| 2011/0290005 | A1* | 12/2011 | Hart | G16H 50/50 73/37.9 |
| 2013/0063570 | A1 | 3/2013 | Michopoulos et al. | |
| 2013/0070074 | A1 | 3/2013 | Won | |
| 2013/0108981 | A1 | 5/2013 | Duret | |
| 2015/0011894 | A1 | 1/2015 | Sarrafzadeh et al. | |
| 2016/0155240 | A1 | 6/2016 | Petiot | |
| 2017/0143208 | A1 | 5/2017 | Blank et al. | |
| 2017/0328794 | A1 | 11/2017 | McLaughlin et al. | |

FOREIGN PATENT DOCUMENTS

| | | |
|---|---|---|
| JP | 2006221031 A | 8/2006 |
| JP | 2012042220 A | 3/2012 |
| JP | 2013538592 A | 10/2013 |
| JP | 2016508783 A | 3/2016 |
| JP | 2018507023 A | 3/2018 |
| KR | 20160084031 A | 7/2016 |
| WO | 2008098339 A1 | 8/2008 |
| WO | 2011154656 A1 | 12/2011 |
| WO | 2014113681 A1 | 7/2014 |
| WO | 2016119011 A1 | 8/2016 |

OTHER PUBLICATIONS

European Patent Office Extended European Search Report for application 19877202.2, mailed on Jul. 7, 2022 (9 pages).
Japanese Patent Office Notification of Decision of Rejection for Application No. 2021-547600, dated Oct. 3, 2023 (7 pages pages with translation).
Lee et al., "Optical-Based Artifical Palpation Sensors for Lesion Characterization", Sensors, 2013, vol. 13, pp. 11097-11113.
Konstantinova et al., "Implementation of Tactile Sensing for Palpation in Robot-Assisted Minimally Invasive Surgery", IEEE Sensors Journal, 2014, vol. 14, No. 8, pp. 2490-2501.
International Search Report and Written Opinion for Application No. PCT/AU2019/051171 dated Dec. 19, 2019 (13 pages).
International Preliminary Report on Patentability for Application No. PCT/AU2019/051171 dated Feb. 16, 2021 (8 pages).
Japanese Patent Office Action for Application No. 2024014216 dated Sep. 6, 2024 (8 pages including English translation).
Korean Patent Office Action for Application No. 1020217014932 dated Nov. 19, 2024 (18 pages including English translation).
Japanese Patent Office Action for Application No. 2024014216 dated Dec. 12, 2024 (8 pages including English translation).

* cited by examiner

OPTICAL PALPATION DEVICE AND METHOD FOR EVALUATING A MECHANICAL PROPERTY OF A SAMPLE MATERIAL

FIELD OF THE INVENTION

The present invention relates generally to a device and a method for evaluating a mechanical property of a sample material using optical palpation, and relates more particularly, although not exclusively, to a digital camera-based optical palpation device and method for characterising an elasticity of the sample material.

BACKGROUND

Elastography techniques based on optical imaging, ultrasound imaging, and MRI are commonly used to measure a deformation in a sample material, such as a biological tissue, and to evaluate stiffness and other mechanical properties of the sample.

In recent years, there has been substantial development in optical coherence tomography (OCT)-based elastography, which provides information to depths up to several millimetres within the sample material with a resolution of a few micrometres. For example, the present applicant has developed an optical palpation (OP) technique, which is disclosed in PCT international patent application no. PCT/AU2016/000019. The disclosed OP technique uses a compliant sensing layer compressed against a surface of a biological sample and uses OCT to measure a change in thickness of the layer introduced by the compression based on forces between the sensing layer and the tissue. OCT-based optical palpation typically relies on interferometry.

The present invention provides further improvement.

SUMMARY OF THE INVENTION

In accordance with a first aspect of the invention, there is provided an optical palpation device for evaluating a mechanical property of a sample material, the device comprising:
  a body having a sensing portion;
  a sensing layer positioned at the sensing portion of the body and having a sensing surface positioned for direct or indirect contact with a surface area of the sample material, the sensing layer being deformable and having a predetermined deformation-dependent optical property; and
  a light detector positioned to detect light transmitted through at least a portion of the sensing layer;
  wherein the optical palpation device is arranged such that, when the sensing surface of the sensing layer is in direct or indirect contact with the surface area of the sample material and a pressure is applied through both the sensing layer and at least a portion of the surface area of the sample material, the sensing layer is deformed and because of the predetermined deformation-dependent optical property of the sensing layer the mechanical property of the sample material is measurable by detecting the light that transmitted through at least a portion of the sensing layer.

Embodiments of the present invention provide a simplified and cost effective optical palpation device. Further the use of the optical palpation device is simplified compared with OCT-based optical palpation devices. The device may be relatively light, handheld and may be arranged for wireless coupling to a computer or the like.

In one specific embodiment the sensing layer is compressible, and the deformation dependent optical property is a compression dependent optical property. The sensing layer may be compressible such that it undergoes minimal lateral expansion upon axial loading.

The deformation-dependent optical property of the sensing layer may be compression-dependent transmissivity, polarisation, light absorption, or light scattering. Alternatively, the deformation-dependent optical property may relate to a wavelengths range of the light that is transmitted at least through a portion of the sensing layer, such that for example the light that is transmitted through at least a portion of the sensing layer has a deformation-dependent colour.

In one example the deformable sensing layer comprises a silicone material and may have air cavities distributed throughout such that the sensing layer has a predetermined opacity.

The light detector may be a camera comprising a charge coupled device (CCD) or a CCD array.

The body may be elongated and may have the sensing portion at one end at which the sensing layer is positioned.

The optical palpation device may be a hand-held device.

The optical palpation device may further comprise a light source for directing light into the sensing layer.

The light source and the light detector may be positioned within the body.

The optical device may further comprise a motion detector for detecting a position of the sensing layer or the device relative to the sample material when the device is moved or scanned relative to a surface of the sample material.

The mechanical property may be elasticity and the detected light may be indicative of a distribution of stress and/or deformation across the sensing layer in response to the applied pressure, the distribution of stress and/or deformation being associated with the mechanical property of the sample material.

In one embodiment, evaluating a mechanical property of the sample material comprises determining a strain of the sample material as a result of the applied pressure.

The optical palpation device may further comprise at least one displacement and force measuring device positioned at the sensing surface of the sensing layer for measuring a force and resultant displacement of regions of the sensing surface. The displacement and force measuring device may comprise an indenter. In one embodiment a plurality of indenters is incorporated into the sensing layer at the sensing surface for contacting the sample material to enable measuring both the force on the sample material and the distance by which the indenter pushes into the tissue.

The sample material may be a biological tissue or a biological material. Alternatively, the sample material may comprise another elastic or deformable material, such as a polymeric material that may have a non-uniform hardness or flexibility.

The optical palpation device may further comprise, when the sensing layer is in indirect contact with the surface area of the sample material, a thin layer such as a transparent sheath to protect the sample material from directly contacting the sensing layer. In one embodiment the sensing layer forms a part of, or is provided in the form of, the sheath.

The light detector may comprise a camera, such as a stereoscopic camera. The light detector may also comprise a smartphone-like device. The smartphone-like device may comprise a detachable micro-lens and/or 3D-printed platform for positioning the sample material.

In one embodiment of the present invention the optical palpation device forms a part of a robotic surgery device.

In another embodiment of the present invention some or all components of the optical palpation device are positioned at or within a balloon catheter arranged such that the optical palpation device can be used to determine a mechanical property of a portion of the sample material within which in use the balloon catheter is positioned. The sensing layer may be positioned outside of, and/or attached to, a balloon of the balloon catheter.

At least some or all components of the optical palpation device may also be positioned at or in a needle, probe or arthroscope, the needle probe or arthroscope having a window at which the sensing layer is positioned such that the mechanical property of the sample material in which the needle, probe or arthroscope is in use positioned can be determined.

The optical palpation device may also comprise a glove and components of the optical palpation device may incorporated into the glove such that optical palpation measurements are possible by a user moving a portion of the glove with the components of the optical palpation device over the material sample when the user wears the glove.

Further, the sensing layer is provided in the form of a lens and the optical palpation device may be arranged for positioning at an eye of a patient and for determining variations in pressure and/or stiffness of the eye.

In accordance with a second aspect of the invention, there is provided an optical palpation device for evaluating a mechanical property of a sample material, the device comprising:
  a body having a sensing portion;
  a sensing layer positioned at the sensing portion of the body and having a sensing surface positioned for direct or indirect contact with a surface area of the sample material, the sensing layer being deformable and having an optically detectable marker or pattern; and
  an optical system capable of providing information that can be used to determine a movement of the marker or pattern relative to the optical system and upon deformation of the sensing layer, the information being provided for a plane orthogonal to a direction of propagation of light;
  wherein the optical palpation device is arranged such that, when the sensing surface of the sensing layer is in direct or indirect contact with the surface area of the sample material and a pressure is applied across both the sensing layer and at least a portion of the surface area of the sample material, the sensing layer is deformed and information concerning the mechanical property of the sample material can be provided by measuring a change in position of the marker or pattern relative to the optical system.

The detectable marker or pattern may be intrinsic to the sensing layer. Alternatively, the detectable marker or pattern may be externally coated, indented or may be a structure created by a light source at the sensing surface of the sensing layer.

In one embodiment the optical system comprises at least two spaced apart light detector components positioned to detect light reflected or transmitted from the marker or pattern. The light detected by each of the at least two detectors may be used to obtain information associated with a depth-distribution of deformation across the sensing layer.

Each light detector may be a camera comprising a charge coupled device (CCD) or a CCD array.

In an alternative embodiment, the optical system comprises an array of optical elements, such as micro lenses, for detecting light transmitted through the sensing layer, and that are positioned such that a depth position of the marker or pattern can be determined. The optical system may comprise a light detector that may be provided in the form of a camera, which may comprise a charge coupled device (CCD) or a CCD array.

The body may be elongated and may have the sensing portion at one end at which the sensing layer is positioned.

The optical palpation device may further comprise a light source for directing light into the sensing layer. The light source and the light detector may be positioned within the body.

The optical palpation device may be a hand-held device.

The optical system comprises a camera, such as a stereoscopic camera. The optical system may also comprise a smartphone-based device. The smartphone-based device may comprise a detachable micro-lens and/or 3D-printed platform for positioning the sample material.

The markers may comprise transparent particles. The markers may also comprise fluorescent particles or photoluminescent particles.

The optical palpation device is arranged such that photographs and mechanical properties of the sample material can be acquired simultaneously.

The optical device may further comprise a motion detector for detecting a position of the sensing layer or the device relative to the sample material when the device is moved or scanned relative to a surface of the sample material.

The mechanical property may be elasticity and the detected light may be indicative of a distribution of stress and/or deformation across the sensing layer in response to the applied pressure, the distribution of stress and/or deformation being associated with the mechanical property of the sample material.

In one embodiment, evaluating a mechanical property of the sample material comprises determining a strain of the sample material as a result of the applied pressure.

In accordance with a third aspect of the present invention, there is provided a system for evaluating a mechanical property of a sample material, the system comprising:
  the optical palpation device in accordance with the first or second aspect of the present invention;
  a processor coupled to the optical palpation device and configured to receive a signal indicative of information associated with the light detected by the light detector;
  wherein the information can be used to obtain a measure of the mechanical property of the sample material.

The system may further comprise a graphical interface, in communication with the processor, and which facilitates forming an image of the sensing layer using the information, the image including features indicative of a distribution of stress and/or deformation across the sensing layer caused by the applied pressure through the sensing layer and through at least the (underlying) sample material.

The processor may be provided in the form of a computer, such as a desktop computer, a mobile phone or any other mobile devices, such as a tablet or any other suitable form.

The processor may be coupled to the optical palpation device in a wired manner or wirelessly, such as using Wi-Fi or Bluetooth technology.

The processor may comprise a graphic processing unit (GPU) and use GPU algorithm to accelerate the processing in order to acquire real-time images of the sensing layer and real-time images including features indicative of a distribution of stress and/or deformation across the sensing layer caused by the applied pressure.

The processor may further be configured to provide augmented reality (AR) or virtual reality (VR) wherein respective real-time images of the sensing layer are overlapped with respective real-time images including features indicative of a distribution of stress and/or deformation across the sensing layer. The respective overlapped images may be projected onto a screen or embedded into a VR goggle, with a corresponding quantitative numerical value of the mechanical property of the sample material indicated.

The processor may be configured to receive a signal from each of at least two spaced apart light detectors, each signal being indicative of information associated with the light detected by the at least two light detectors. The respective signals may be used to form an optical image of the sensing layer using the graphical interface, the optical image including features indicative of a depth-distribution of deformation across the sensing layer. Further, the processor may be configured to control the light detector, which may be an image detector, to take a sequence of images at a predetermined frequency when the device is stationary or when the device is moved or scanned across the sample material.

Further, the processor may be arranged to receive signals from the motion detector for detecting a (change of) position of the sensing layer or the device relative to the sample material when the device is moved or scanned relative to a surface of the sample material, such that a map or scan of the distribution of the deformation of the sensing layer can be formed using the sequence of images and the information from the motion detector when the device is moved or scanned across the sample material.

In accordance with a fourth aspect of the present invention, there is provided method for evaluating a mechanical property of a sample material, the method comprising:
providing the sample material;
providing a system in accordance with the third aspect;
the method further comprising:
    positioning the sensing layer relative to the sample material such that the sensing surface is in direct or indirect contact with a surface area of the sample material;
    applying a pressure through both the sensing layer and at least a portion of the surface area of the sample material; and
    detecting light transmitted or reflected from at least a portion of the sensing layer.

The processor of the system in accordance with the third aspect of the present invention may further be arranged to receive a signal indicative of a position of the sensing layer or the optical palpation device relative to the sample material.

In one embodiment, the method comprises providing a graphical interface in communication with the processor for forming an image of the sensing layer using the information, the image including features indicative of a distribution of stress and/or deformation across the sensing layer caused by the applied pressure through the sensing layer and through at least a portion of the underlying surface area of the sample material.

The processor may be provided in the form of a computer, such as a desktop computer, or a mobile phone or any other mobile devices, such as a tablet.

The method may further comprise determining a strain of the sample material as a result of the applied pressure so as to evaluate the mechanical property of the sample material.

The strain of the sample material may be determined by analysing, using the microprocessor or GPU, a pixel distribution in the formed optical image.

In accordance with a further embodiment of the present invention, the method comprises:
    providing a motion detector for detecting a position of the sensing layer or the device relative to the sample material when the device is moved or scanned relative to a surface of the sample material;
    moving the optical palpation device across a plurality of surface areas of the sample material while (i) applying a pressure through both the sensing layer and at least a portion of a respective surface area of the sample material such that the sensing layer is compressed and (ii) either simultaneously detecting light transmitted through, or reflected from, at least a portion of the sensing layer for each of the plurality of surfaces areas of the sample material, or sequentially detecting light during movement of the device across the sample material; and
    detecting a movement or change in coordinates of the sensing layer or the device relative to the sample material.

The method may further comprise using the processor and graphical interface for assembling a sequence of images in accordance with the detected movement or change in coordinates so as to obtain a stress map indicative of a distribution of stress across the sensing layer in relation to the plurality of surface areas of the sample material.

In one embodiment, the method may comprise providing an optical palpation device comprising at least two light detectors positioned for detecting light transmitted or reflected through the same portion of the sensing layer so as to obtain information associated with a depth-distribution of deformation across the sensing layer.

The method may further comprise forming a strain image indicative of a depth-distribution of deformation and incorporating the strain image with the stress map indicative of a distribution of stress across the sensing layer and display both the strain image and the stress map in AR or VR devices, such as VR goggles.

In one specific embodiment the optical palpation device comprises a camera and a motion detector for detecting a position or motion of the sensing layer or the device relative to the sample material, the method comprising:
    providing a motion detector for detecting a position of the sensing layer or the device relative to the sample material when the device is moved or scanned relative to a surface of the sample material; wherein
    the step of applying a pressure through both the sensing layer and at least a portion of the surface area of the sample material comprises applying varying different pressures through both the sensing layer and at least a portion of the sample material, comprising moving a portion of the optical palpation device with the sensing layer relative to the material sample to apply the varying different pressures; wherein
    the step of detecting light transmitted or reflected from at least a portion of the sensing layer is conducted using the camera and while the varying different pressures are applied such that images are detected for a sequence of pressures; wherein
    the mechanical property, such as stress, of the sample material can be determined from the change in optical property of the sensing layer detected with the images recorded for the sequence of pressures; and wherein strain of the material sample can be determined from a determined movement of the probe relative to the material sample, the movement being determined using the provided motion detector;

whereby a non-linear mechanical property of the material sample can be determined.

The invention will be more fully understood from the following description of specific embodiments of the invention. The description is provided with reference to the accompanying drawings.

BRIEF DESCRIPTION OF DRAWINGS

Notwithstanding any other forms which may fall within the scope of the disclosure as set forth in the Summary, specific embodiments will now be described, by way of example only, with reference to the accompanying drawings in which.

DETAILED DESCRIPTION OF SPECIFIC EMBODIMENTS

Figure 1:
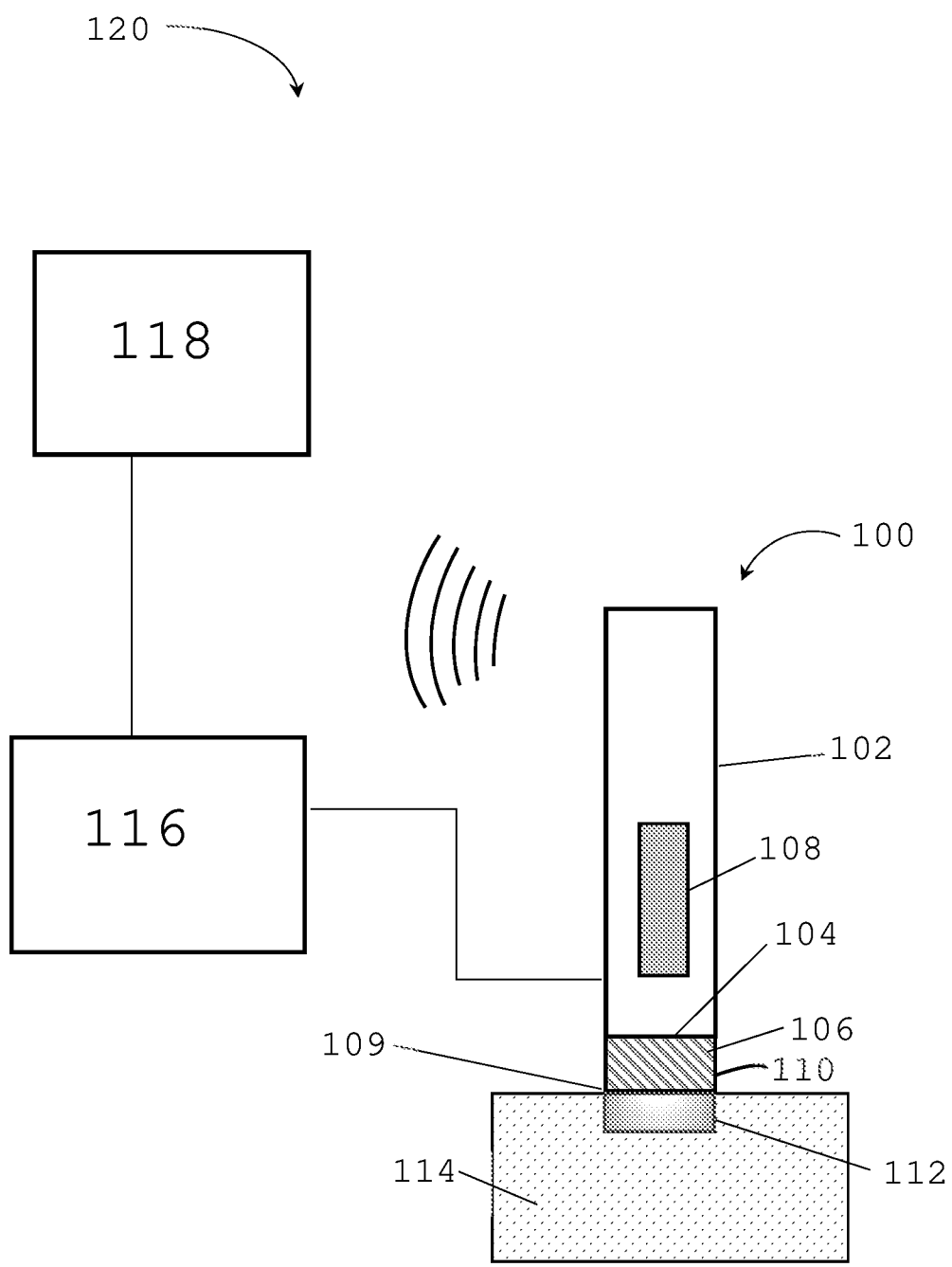
FIG. 1 shows an optical palpation device in accordance with an embodiment of the present invention.

Embodiments of the present invention relate to a device and a method for evaluating a mechanical property of a sample material using optical palpation.

Optical palpation is a technique that can be used to map surface stress of a sample material, such as a biological tissue or biological material, wherein a compressive load is applied to a sensing layer positioned against the sample material. It is known to have a deformable sensing layer comprising a transparent silicone material and being incompressible such that it compresses and deforms under the application of the compressive load by expanding in a plane transversal to the applied load to preserve its volume. The thickness of the sensing layer thus changes in response to the local stiffness of the underlying material and OCT is typically used to measure and image the change in thickness introduced by compression to the sensing layer placed on the sample material. The OCT image encodes a stress distribution or stress map of the sensing layer, which is related to the surface stress of the sample material. OCT-based optical palpation typically requires depth scanning (or depth sectioning) of the entire thickness of the sensing layer so as to obtain information relating to a depth distribution of deformation and further determine strain experienced by the sensing layer. The stress experienced by the sensing layer can then be determined based on the determined strain and a known stress-strain curve of the material of the sensing layer. The elasticity of the sample material can then be quantitatively determined using the determined stress and strain.

The present invention proposes a simplified optical palpation technique that allows obtaining a measure of the surface stress experienced by the sensing layer (and indicative of the stress at the surface of the sample material) and subsequently allows evaluating a mechanical property of the sample material without the need for OCT depth scanning.

In accordance with embodiments of the present invention, the optical palpation device and optical palpation method are digital camera-based. The mechanical property relates to the elasticity or stiffness of the sample material, and the sample material may be a biological tissue whereby the method and device may be used specifically for medical applications, such as cancer margin imaging wherein information about location and size of a tumour can be obtained for a treatment of cancer, or such as scar assessment in dermatology. In the medical field, it is indeed known that abnormalities such as diseased tissue may alter the elasticity of biological tissue. For example, cancerous tissue is typically "stiffer" than surrounding healthy soft tissue. The sample material may alternatively be a biological material such as a food material wherein an application may be food quality monitoring. In another embodiment, the sample material may be any elastic or deformable material, such as a polymeric material that may have a non-uniform hardness or flexibility. For example, a non-medical application may be textile sensing wherein the sample material may comprise rubber or gels.

It will further be understood by the person skilled in the art that other sample materials may be considered, as well as other applications, and other mechanical properties may be evaluated such as viscoelasticity, or even non-linear mechanical properties.

In one specific embodiment, the proposed technique uses a sensing layer that is deformable and is compressible. The sensing layer has a predetermined optical property that changes upon application of a pressure or load on at least a surface portion of the sensing layer and subsequent compression of the sensing layer, i.e. the sensing layer comprises a material having a predetermined optical property that is compression-dependent.

The use of a sensing layer that is compressible is advantageous for the following reason. The application of a load on a surface of the compressible sensing layer results in the sensing layer being compressed without expanding in a lateral direction, i.e. the sensing layer does not expand in a plane transversal to the applied load, wherein a volume of the sensing layer is not preserved. As a result, any friction and/or surface roughness that is likely to occur when using an incompressible sensing layer can be substantially reduced and a sharper change in thickness of the sensing layer as a function of different 'stiffness' of the underlying sample material may be observed and measured. The effective spatial resolution of the optical palpation technique can subsequently be improved, which may further allow improving an accuracy with which the mechanical property can be determined.

Referring to FIG. 1, the optical palpation device 100 in accordance with a specific embodiment of the present invention is a hand held device 100 in the shape of a pen comprising a body 102 having a sensing portion 104, a sensing layer 106 that is positioned at the sensing portion 104, and a light detector 108 that is positioned such that, in use, light transmitted through the sensing layer 106 can be detected. In the present embodiment, the body 102 is elongated and comprises the light detector 108, which is provided in the form of a camera, such as a digital charge coupled device (CCD) camera. The sensing layer 106 is compressible, has a compression-dependent optical property, and is preferably rigidly fixed to the sensing portion 104 at an end 109 of the elongated body 102. The sensing portion 104 is preferably an imaging window that is fixed to the end 109 of the elongated body 102 and can be easily replaced if broken or scratched. The sensing layer 106 has a sensing surface 110 positioned for direct contact with a surface area 112 of a sample material 114. Alternatively, the sensing surface 110 may be in indirect contact with the sample material 114 and a thin layer (not shown) comprising latex or another plastic material, such as a compliant transparent surgical sheath, may for example be positioned between the sensing surface 110 and the sample material 114 for preventing contamination of the biological tissue and ensuring sterile conditions. The camera 108 is typically positioned such that the working distance between the camera 108 and the surface area 112 of the sample material 114 corresponds approximately to a couple of centimetres. The optical palpation device 100 is arranged such that, when the sensing surface 110 of the sensing layer 106 is in contact with the surface area 112 of the sample material 114 and a pressure is applied across both the sensing layer 106 and at least a portion of the surface area 112 of the sample material 114, the sensing layer 106 is compressed and the predetermined compression-dependent optical property of the sensing layer 106 influences the light within the sensing layer 106 such that the light detected by the camera 108 is a measure for the mechanical property of the sample material 114.

In a specific embodiment of the present invention, as illustrated in FIGS. 2a-2h, the compression-dependent optical property of the sensing layer 106 is compression-dependent transmissivity. The sensing layer 106 is configured to be opaque when no compression is applied and to become more transparent upon application of a pressure, i.e. upon application of a pressure across the sensing layer 106, more light is being transmitted through the sensing layer 106.

Figure 2:
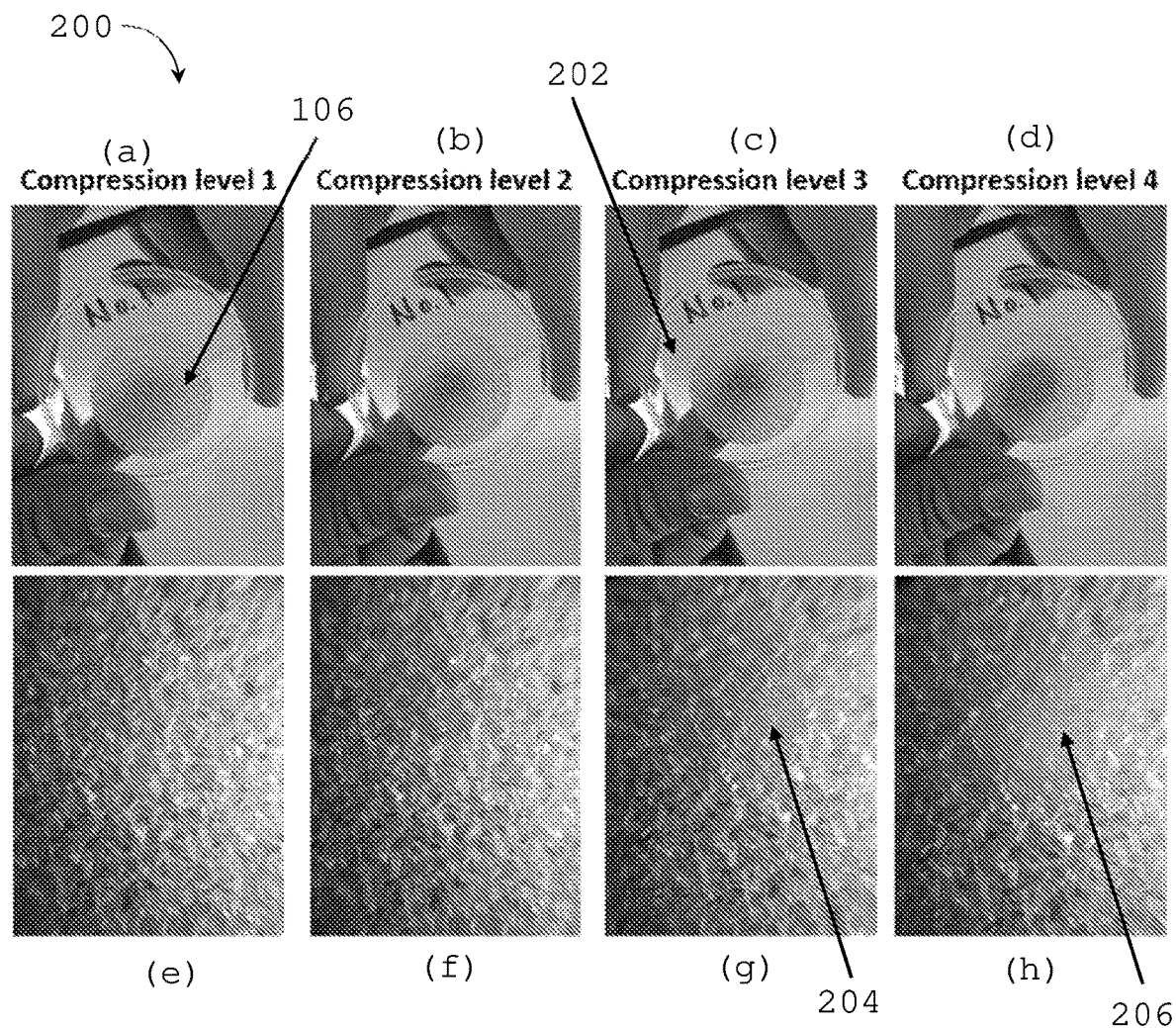
FIGS. 2a-2h show pictures illustrating the influence of a given compression of a sensing layer on the transmission of light through a sensing layer in accordance with embodiments of the present invention.

Referring to FIGS. 2a-2h, there is shown an illustration 200 of how a load applied at different pressure levels influences the light within the sensing layer 106. Specifically, FIGS. 2a-2d correspond to images illustrating the simulation of the application of a load with increasing pressure across the sensing layer 106 using a finger. The sensing layer 106 is fixed to a glass plate 202, such as by means of a glue, such that the sensing layer 106 does not 'slip' or move relative to the glass plate 202, and such that application of a load can essentially result in a compression of the sensing layer 106 along a thickness of the sensing layer 106 and does not result in any lateral movement of the sensing layer 106. FIG. 2a corresponds to the application of a load with the lowest pressure, while FIG. 2d corresponds to the application of a load with the highest pressure. FIGS. 2e-2h are images formed using a digital CCD camera and relate to FIGS. 2a-2d, respectively. It can be seen that as the load is applied with increasing pressure, the sensing layer 106 becomes more transparent within the region of the applied load, i.e. where the finger applies pressure, such as at areas 204 and 206 in FIGS. 2g and 2h.

In a specific embodiment, the sensing layer 106 comprises a mixture of sugar and silicone and is fabricated according to a method that allows achieving a particular opacity in a state for which no compression is applied to the sensing layer. Sugar is mixed with silicone as the silicone cures and the sugar is subsequently dissolved out with water so as to obtain a sensing silicone layer 106 having air cavities distributed throughout, the sensing layer 106 having a texture similar to the one of a sponge. The air-silicone interfaces within the sensing layer 106 cause reflections of light and provide the initial opaque appearance of the sensing layer 106 as no compressive load is applied. FIGS. 2a and 2e illustrate an example of the opacity of the sensing layer 106 as very little pressure is applied to the sensing layer.

The application of a compressive load to a surface area of the sensing layer 106 results in the compression and closure of the air cavities within the sensing layer 106, whereby an increased amount of light is enabled to be transmitted through the sensing layer 106. By placing a digital camera in proximity to the surface of the sensing layer 106 which is not in contact with a surface of the sample material 114, i.e. in proximity to the surface opposite the sensing surface 110 of the sensing layer 106, a change in the light detected by the digital camera is directly related to the stress at the surface area 112 of the sample material 114. The presence of air cavities in the sensing layer assist in providing the property of compressibility of the sensing layer, i.e. a sensing layer characterised by a relatively low Poisson's ratio, wherein the tendency of the sensing layer to expand in directions transversal to direction of compression is relatively minimised.

The sensing layer 106 may have any dimensions appropriate for being fixed to a given sensing portion of a body portion of an optical palpation device in accordance with embodiments of the present invention. In the specific embodiment of a pen-shaped optical palpation device 100, it is envisaged that the sensing layer 106 be cylindrical in shape with a diameter of approximately 10 mm and a height of approximately 1 mm. However, it will be understood that any other shape and/or dimensions are further envisaged.

The camera-based optical palpation device 100 is coupled wirelessly, such as using Wi-Fi or Bluetooth, to a microprocessor 116 in communication with a graphical interface 118, whereby a system 120 for evaluating a mechanical property of the sample material 114 is formed. The microprocessor 116 may be provided in the form of a computer such as a desktop computer, or in form of a mobile device, such as a tablet or a mobile phone. The microprocessor 116 is configured to receive, in use, an electrical signal from the optical palpation device 100, the signal being of information associated with the light detected by the CCD camera 108. The information can then be used by the microprocessor 116 and the graphical interface and be converted into an image. The image may be of the type as illustrated in FIGS. 2e-2h and is indicative of a distribution of stress and deformation across the sensing layer 106, in relation with the surface area 112 of the sample material 114 being affected by the applied pressure.

The implementation of the device 100 as a handheld pen-shaped device 100 wirelessly connected to a microprocessor 116 and graphical interface 118 allows providing a compact optical palpation device with increased usability. The handheld pen-shaped optical palpation device 100 can, for example, reach remote areas of a sample material, which is particularly advantageous for medical applications to reach areas of a biological tissue not easily accessible using conventional OCT-based optical palpation systems or devices. In addition, the cost associated with the optical palpation device defined in accordance with embodiments of the present invention is substantially lower than the cost associated with conventional OCT-based optical palpation devices.

It will be understood that the camera-based optical palpation device 100 may however alternatively be wired to the microprocessor 116 in communication with the graphical interface 118.

It will also be understood that it is envisaged, in an alternative embodiment, to use a sensing layer configured to have other compression-dependent optical properties, and for example be transparent when no compression is applied and become increasingly turbid upon the application of pressure. Further, in other embodiments, the sensing layer may have a predetermined compression-dependent light polarisation, light absorption or light scattering property.

In an alternative embodiment, it is also envisaged to have a sensing layer that is deformable however not compressible, and having a predetermined deformation-dependent optical property wherein the sensing layer comprises a material that changes colour upon application of a pressure, wherein a change in colour could, in use, be detected by the digital camera 108 and used to form an image indicative of a distribution of stress and deformation across the sensing layer 106 related to the stress at the surface area 112 of the sample material 114. In order to evaluate the elasticity of the sample material 114 at the surface area 112, strain across the sensing layer 106 as a result of the application of the load needs to be determined, by either directly or indirectly measuring a change in thickness of the sensing layer 106 as a result of the applied load.

Strain may be indirectly determined by using the formed image. In this embodiment, the compression-dependent optical property of the sensing layer 106 is calibrated such that a change in the light intensity detected by the light detector 108 (in the embodiment in which the compression-dependent optical property is compression-dependent light transmissivity) can be associated to a value of strain. As a result, changes in the light detected by the light detector 108 can be used as a measurement of strain experienced by the sensing layer 106.

Alternatively, strain and elasticity of the sample material 114 at the surface area 112 may be directly quantitatively evaluated using an indenter or an array of indenters placed at the sensing surface 110 of the sensing layer 106 in contact with the surface area 112 of the sample material 114. The small indenters allow measuring a depth of displacement of the sensing surface 110 along a thickness of the sensing layer 106 upon application of the pressure, which relates to the displacement of the surface area 112 of the sample material 114 in a direction transversal to the applied load.

The strain ε experienced by the sensing layer 106 as a result of the application of the pressure can generally be determined as follows:

$$\varepsilon = \frac{\Delta L - \Delta L_0}{\Delta L_0}$$

wherein ε relates to the strain of the sensing layer 106, ΔL relates to the depth of displacement of the sensing surface 110 in a direction transversal to the applied load and resulting change in thickness of the sensing layer 106 due to application of the pressure. $\Delta L_0$ relates to an initial thickness of the sensing layer 106 before application of the suitable load. Specifically, in the present embodiment for which the sensing layer 106 is compressible and has a predetermined compression-dependent optical property, a calibration is used to correlate a depth of displacement of the sensing surface 110 to a change in the thickness of the sensing layer 106 as compared to the initial thickness of the sensing layer 106 as a result of the applied load.

As a measure of the elasticity of the sample material 114 at the area of the surface area 112, the Young's modulus E of the sample material 114 can typically be quantitatively determined according to equation (1):

$$E = \frac{\sigma_{sensing\ layer}}{\varepsilon_{sample\ material}} \quad (1)$$

Wherein E relates to the Young's modulus of the silicone sample, $\sigma_{sensing\ layer}$ relates to stress determined across the sensing layer 106, and $\varepsilon_{sample\ material}$ relates to strain distributed within the sample material at the area of the surface area 112.

In the embodiment using an indenter placed at the sensing surface 110 of the sensing layer 106 in contact with the surface area 112 of the sample material 114, a quantitative measure of the elasticity of the sample material 114 can more specifically be determined according to the following equation (2):

$$\frac{1}{E_r} = \frac{1 - v_i^2}{E_i} + \frac{1 - v_s^2}{E_s} \quad (2)$$

Where $E_r$ is the reduced modulus of the sample material 114, i.e. a combination of the sample material 114 and indenters elastic deformations, $E_s$ and $v_s$ are, respectively, the Young's modulus and Poisson's ratio of the sample material 114, and $E_i$ and $v_i$ are, respectively, the Young's modulus and Poisson's ratio of the indenter. In this equation, $E_i$ and $v_i$ can be characterised preliminarily, $v_s$ can be estimated for most solid materials, and $E_r$ can be expressed as:

$$E_r = \frac{\sqrt{\pi}\, S}{2\beta \sqrt{A_p(h_c)}}$$

where $A_p(h_c)$ is the projected area of the indentation at the contact depth $h_c$, $A_p(h_c)$ can be calculated based on the indenter geometry; β is a pre-known geometrical constant; S is the stiffness of the contact which can be indicated from the stress-displacement curve upon unloading of the indenter, with both stress and displacement of the indenter tip contacting the sample material measurable from our device and method. As such, $E_r$ is a measurable parameter in Eq. (2). By substituting $E_r$, $E_i$, $v_i$ and $v_s$ into Eq. (2), the value of Young's modulus of the sample $E_s$ can be derived.

In addition, a light source (not shown) may be provided within the body 102 for directing light into the sensing layer. The camera 108 within the body 102 is then configured to capture light transmitted by the sensing layer 106 in response to receiving the light from the light source.

In accordance with another specific aspect of the present invention, the sensing layer 106 is deformable or moveable and may be incompressible. The sensing layer 106 comprises an optically detectable marker or pattern that is printed on the sensing surface 110 of sensing layer 106. Alternatively, the marker or pattern may be in the form of a coating or indent in the sensing surface 110 of sensing layer 106 or may be created by a light source projecting a given light structure or pattern onto the sample material.

Figure 3:
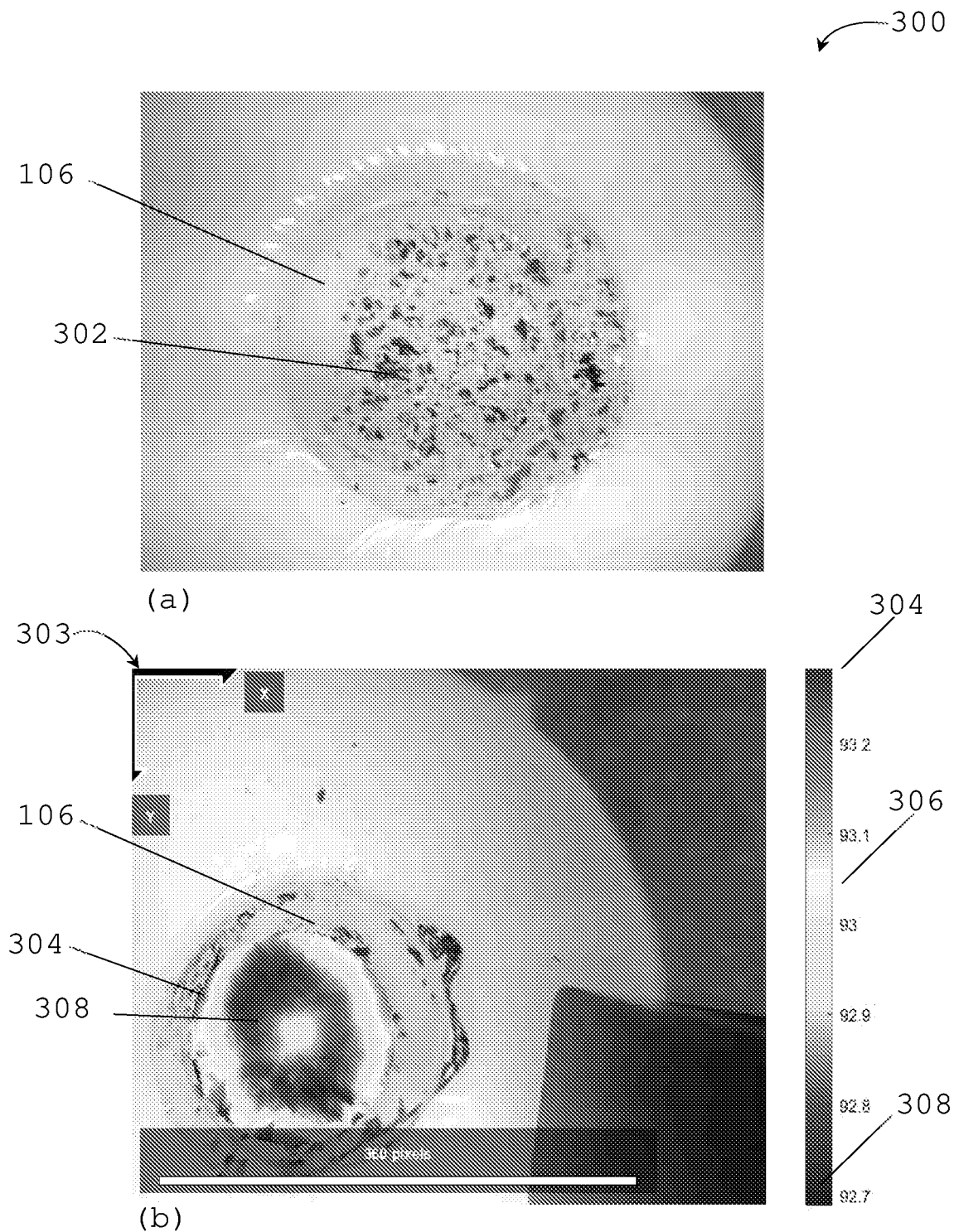
FIG. 3(a) shows a picture of a sensing layer used for evaluating a mechanical property of a sample material in accordance with the further embodiments of the present invention.
FIG. 3(b) shows a picture indicative of a depth distribution of deformation with the sensing layer shown in FIG. 7(b) using the optical palpation system in accordance with the further embodiments of the present invention.

Referring to FIG. 3(*a*), there is shown a picture 300 of a sensing layer 106 comprising a speckle pattern 302.

In this embodiment, the optical palpation device 100 comprises an optical system capable of providing information that can be used to determine a movement of the marker or pattern, such as a speckle pattern 302, relative to the optical system upon deformation of the sensing layer 106 in response to the applied load.

Figure 4:
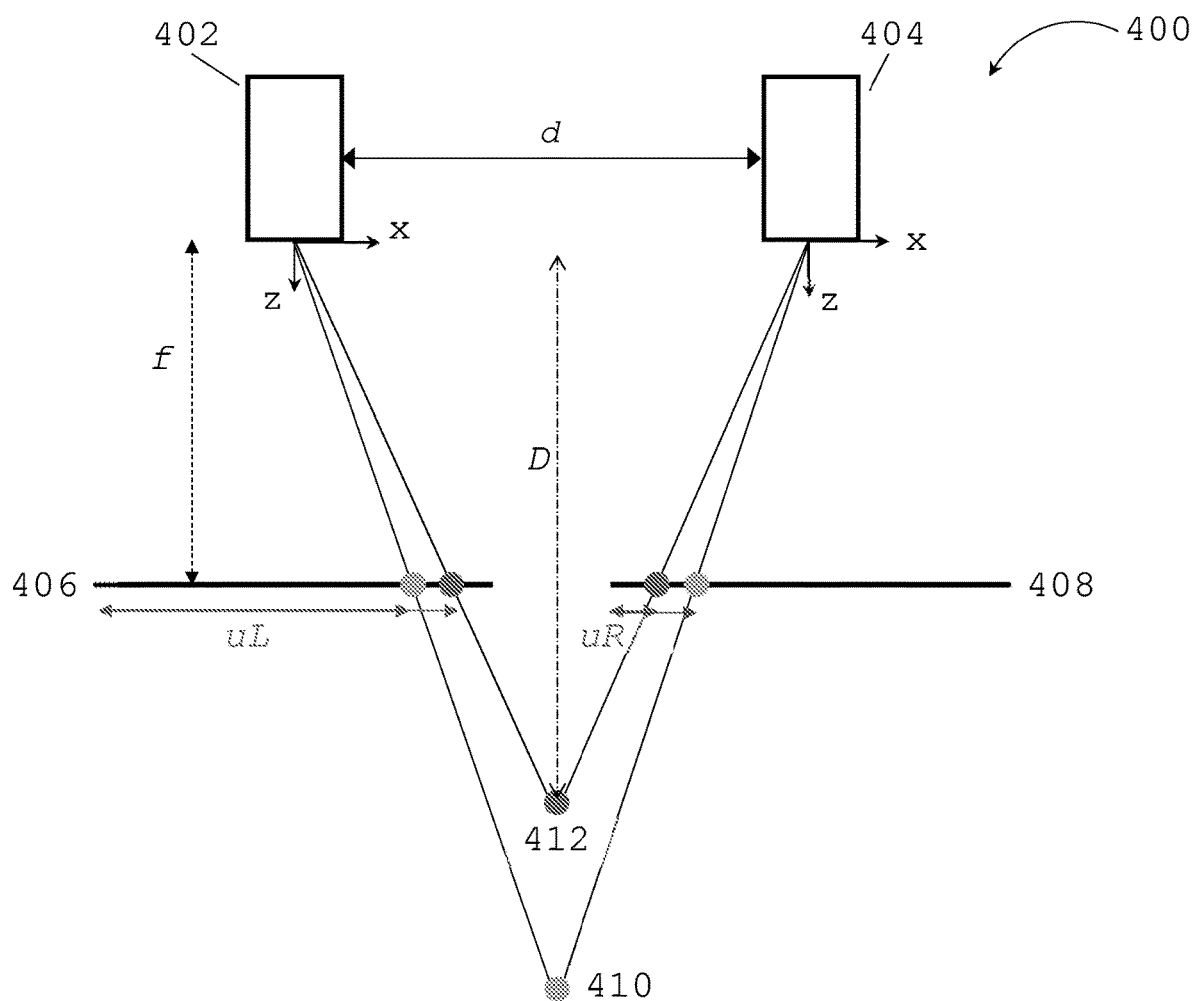
FIG. 4 shows a schematic representation of an optical system used for evaluating a mechanical property of a sample material in accordance with a further embodiment of the present invention.

The optical system in this embodiment comprises two spaced apart light detectors, such as two spaced apart light detectors 108. Referring to FIG. 4, there is shown a stereoscopic optical system 400 of the optical palpation device 100 in accordance with this specific embodiment of the present invention. The optical system 400 comprises two light detectors 402, 404 provided in the form of cameras spaced apart by a distance d and positioned to detect light reflected or transmitted from the speckle pattern 302 in a plane orthogonal to a direction of propagation of the light. The optical system 400 seeks to create a stereoscopic vision so as to simulate the binocular vision of two eyes, which further allows, in use, obtaining information as to the depth of the features of deformation distributed across the sensing layer 106 upon application of the pressure.

In this embodiment, a microprocessor similar to microprocessor 116 receives information from the two cameras 402, 404, and two respective images of the surface areas 406, 408 of the sensing surface 110 of the sensing layer 106, can be formed associated with the cameras 402, 404, respectively. The speckle pattern 302 is arranged such that it can be relatively well recognised and co-registered by the two cameras 402, 404, and such that a correlation between the two images can be obtained. As the features in a speckle pattern are unique everywhere, a minimal co-registering error can be achieved by a simple correlation algorithm.

As can be seen in FIG. 4, in the stereoscopic vision, an element located at a relatively far distance D from the cameras 402, 404 will result in a focus on the two corresponding light detectors with a small coordinate difference or small disparity as indicated in FIG. 4 by the 'uL-uR' segments relating to the point 410 at the furthest distance from the surface areas 406, 408. In contrast, an element located at a relatively closer distance D from the cameras 402, 404 will result in a focus on the two corresponding light detectors with a high coordinate difference or high disparity as indicated by the 'uL-uR' segments relating to the point 412. A co-registration of the two images obtained from the cameras 402, 404 respectively allows obtained a disparity map, which is a direct qualitative indication of the depth-distribution of elements of deformation within the sensing layer 106.

FIG. 3(*b*) shows an image 303 indicative of a depth-distribution of deformation obtained using the sensing layer 106 of FIG. 3(*a*) and the optical system of FIG. 4. The depth-distribution of deformation is represented qualitatively in the form of a colour scale, wherein the red end 304 of the colour scale 306 indicates that a corresponding portion of the sensing layer 106 experiences a more pronounced deformation as a result of the applied load in comparison with the blue end 308 of the colour scale 306 that indicates that a corresponding portion of the sensing layer 106 experiences a less pronounced deformation as a result of the applied load.

An analysis of pixel distribution of the image 300 performed using a digital image processing algorithm allows obtaining quantitative depth information of elements of deformation within the sensing layer 106, which relates to the strain experienced by the sample material 114 at the surface area 112.

The stereoscope comprising the cameras 402, 404, may for example be made by some off-the-shelf components, such as USB endoscopic cameras. A 3D printing technique may be used to customise a form or shape of the stereoscope, for example a 3D printed casing for supporting the two cameras 402, 404.

It will be understood that although the present embodiment illustrated in FIG. 4 has been illustrated in regard to two cameras 402, 404, more than two cameras may be used, which may allow obtaining more accurate information to constrain a depth-distribution of deformation across the sensing layer 106.

Further, it is envisaged in one embodiment that the light detector of the optical palpation device, such as light detector 108 of optical palpation device 100, be provided in the form of a camera of a smartphone device or other smartphone-based device. In the embodiment of the optical palpation device 100 comprising the optical system 400, it is also envisaged that the optical system 400 comprise a smartphone-based device. In these embodiments, the smartphone-based device may further be equipped with a detachable micro-lens and/or 3D-printed platform for positioning the sample material.

Figure 5:
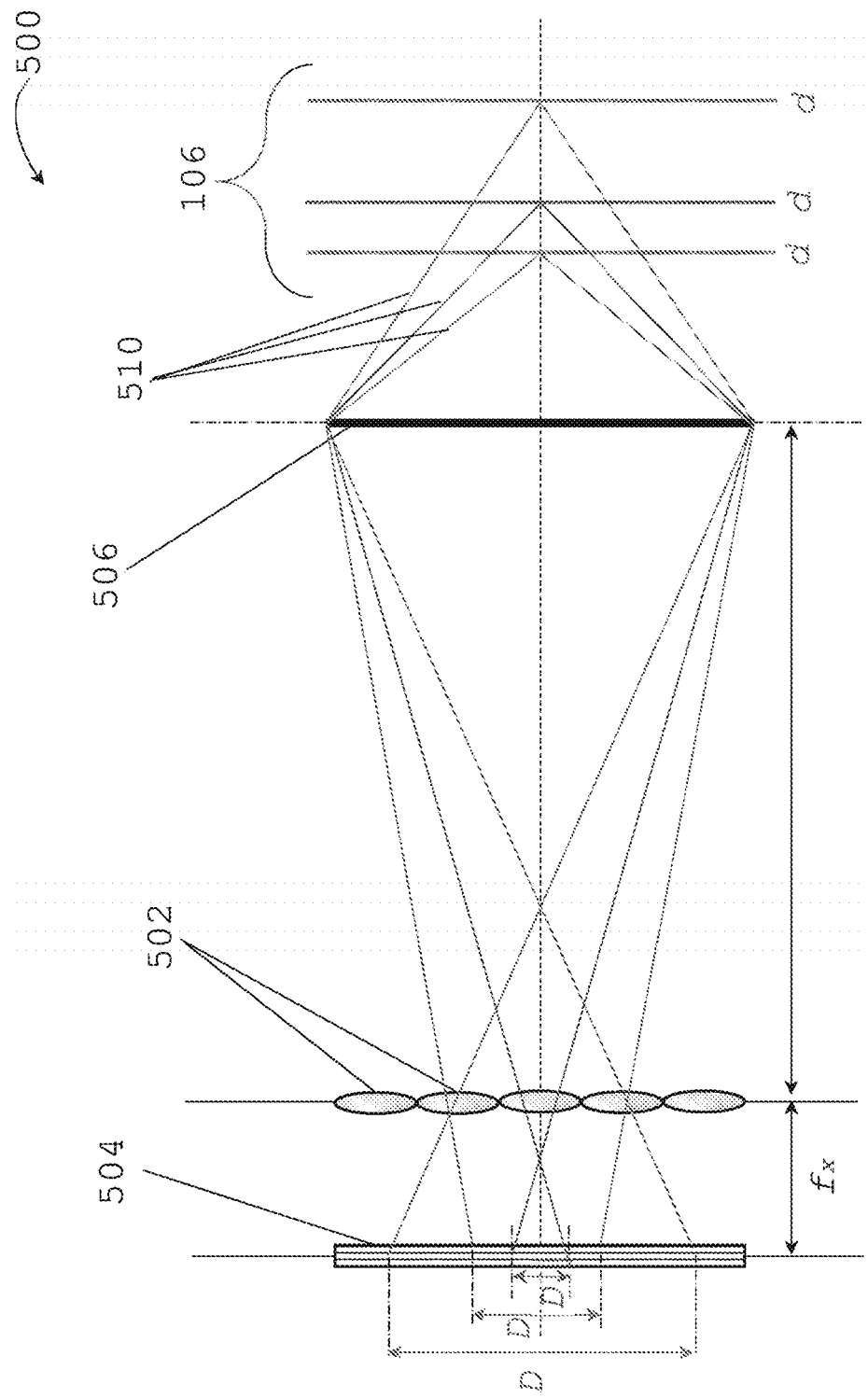
FIG. 5 shows a schematic representation of an alternative optical system used for evaluating a mechanical property of a sample material in accordance with the further embodiment of the present invention.

Referring to FIG. 5, there is shown an alternative optical system 500 that can be used to obtain a direct indication of a depth-distribution of elements of deformation within the sensing layer 106 (deformable or movable, incompressible and comprising a speckle pattern). The optical system 500 comprises an array of micro lenses 502 for detecting light transmitted through the sensing layer, the micro lenses 502 being positioned such that a depth position d of elements of the speckle pattern can be determined. The optical system 500 allows performing a light-field imaging of the deformable incompressible sensing layer 106, wherein an image can be formed, the image being indicative of a depth-distribution of elements of deformation within the sensing layer 106. The optical system 500 further comprises a light detector 504, a mains lens 506 positioned at the sensing portion, similar to the sensing portion 104 of optical palpation device 100. The micro lenses 502 are positioned at a distance din from the main lens 506 and a position $f_x$ from the light detector 604. As can be seen in FIG. 5, the lateral location and angle of each light ray 510 transmitted through the sensing layer 106 can be detected by the light detector 504 by means of the micro lenses 502. Similarly, to the telescopic optical system 400, elements positioned at different distances d, d', d" from the light detector 504 will result in different pixel distribution D, D', D" of these elements and the depth information can be obtained by analysing the pixel distribution in a formed image using digital image processing, for example. As for the embodiment of the stereoscopic optical system 400, the speckle pattern of the sensing layer can be relatively well recognised and co-registered by the micro lenses 502 and light detector 504.

Figure 6:
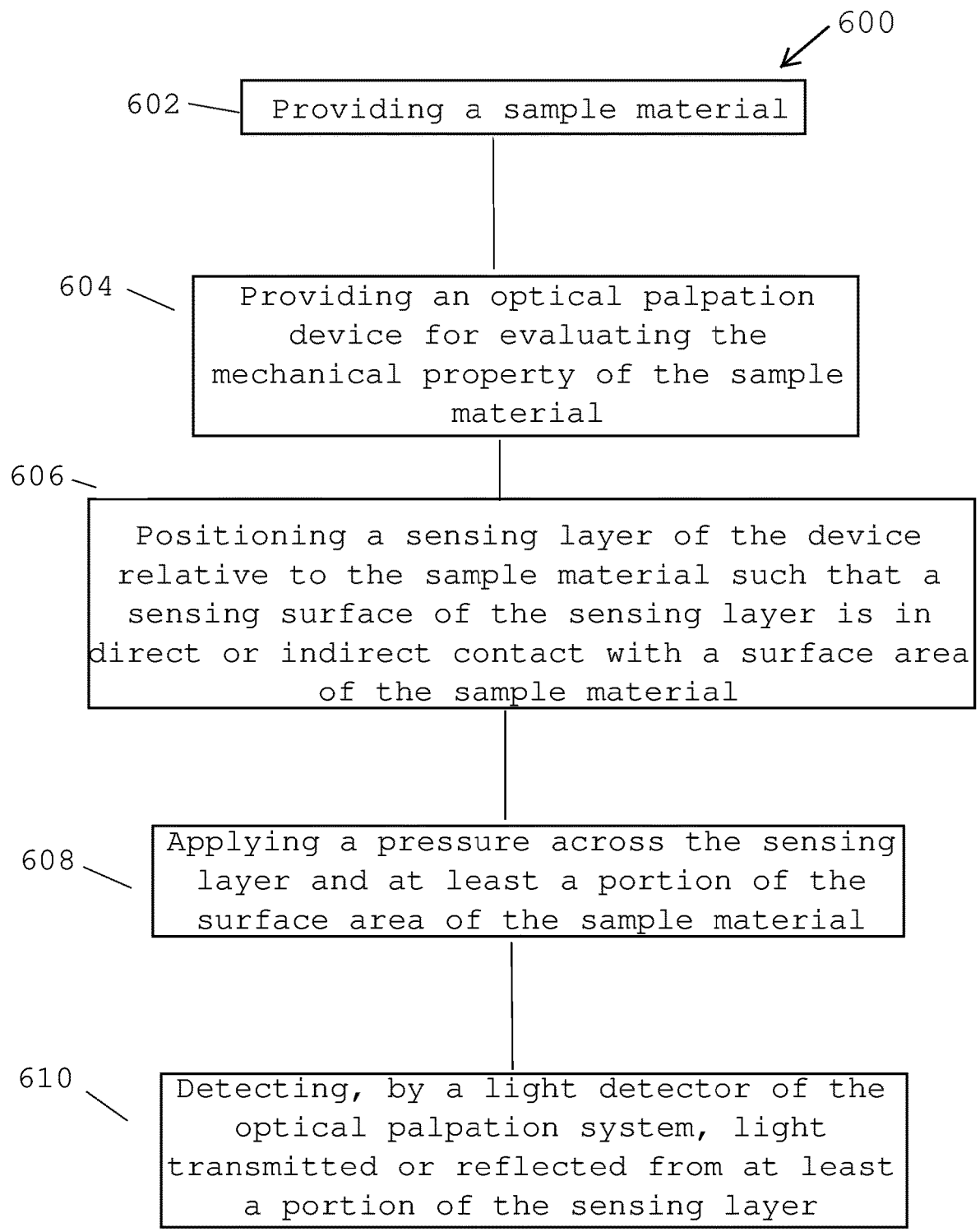
FIG. 6 shows a flow chart of an optical palpation method of evaluating a mechanical property of a sample material in accordance with an embodiment of the present invention.

Referring to FIG. 6, there is shown a flow chart of a camera-based optical palpation method 600 for evaluating a mechanical property of a sample material in accordance with a specific embodiment of the present invention.

Similar to the OCT-based optical palpation technique, the present method allows obtaining information relating to the elasticity of the sample material 114. The present method is however substantially simplified as it can be implemented using a compact system and device and can also be implemented wirelessly, which may be advantageous in particular for medical applications to biological tissue as it may allow reaching areas of a sample material otherwise relatively difficult to access.

At step 602, a sample material, such as sample material 114 is provided. In a specific embodiment, the sample material 114 is a biological tissue. However, as mentioned above, the sample material 114 may alternatively be a biological material or any elastic or deformable material, such as a polymeric material that may have a non-uniform hardness or flexibility, for example.

At step 604, an optical palpation device is provided such as optical palpation device 100 or optical palpation device comprising the optical system 400 or 500 for evaluating the mechanical property of the sample material 114.

At step 606, the sensing layer 106 is positioned relative to the sample material 114 such that the sensing surface 110 is in direct contact with the surface area 112. It will be appreciated that the sensing layer 106 may alternatively be positioned such that the sensing surface 110 is in indirect contact with the surface area 112, for example using a thin layer (not shown) comprising latex or another plastic material, such as a surgical sheath, positioned between the sensing surface 110 and the sample material 114 for preventing contamination of the biological tissue and ensuring sterile conditions.

At step 608, a pressure is applied across the sensing layer 106 and across at least a portion of the surface area 112 of the sample material 114.

At step 610, the light detector 108 of optical palpation device 100, or light detectors 402 and 404 of optical system 400, or light detector 504 of optical system 500, detects light transmitted or reflected from at least a portion of the sensing layer 106. The detected light is a measure for the mechanical property of the sample material. In particular, the detected light is used to determine a distribution of stress and/or deformation across the sensing layer 106 in response to the applied pressure.

A microprocessor 116 in communication with a graphical interface 118 is further provided, in the form of a computer, such as a desktop computer, or any mobile device, such as a tablet or a mobile phone. The microprocessor 116 is coupled to the optical palpation device 100 and is configured to receive an electrical signal from the device 100, the signal being indicative of information associated with the light detected by the light detector 108. The received signal and corresponding information are then used by the graphical interface 118 to form an image of the sensing layer 106. The image includes features that are indicative of a distribution of stress and/or deformation across the sensing layer 106 caused by the applied pressure through the sensing layer 106 and through at least a portion of the underlying surface area 112 of the sample material 114. The distribution of stress and/or deformation therefore relates to the surface area 112 of the sample material 114 being affected by the applied pressure. The microprocessor 116 can then further be used to perform an analysis of the pixel distribution across the optical image to quantify the strain of the sample material 114 at the surface area 112.

The optical resolution of the measurements typically depends on how the deformation-dependent optical property of the sensing layer 106 influences the light transmitted through the sensing layer 106, and more specifically on the dynamic range of the deformation-dependent optical property. Further, the optical resolution of the measurements depends on the sensitivity of the camera 108 to detect changes in the light transmitted through the sensing layer 106, or on the sensitivity of the cameras 402, 404 or light detector 504 to co-register the features of the speckle pattern.

The optical resolution provided by conventional OCT-based optical palpation devices is typically in the range between 100 µm and 200 µm. In accordance with embodiments of the present invention, the optical resolution of the camera-based optical palpation device may vary between 10 µm and 200 µm depending on the resolution of the optical system used and on the physical deformation of the sensing layer 106. In particular, in accordance with the embodiment in which the sensing layer 106 is compressible, i.e. wherein transverse motion of the sensing layer 106 is restricted, an optical resolution of the camera-based optical palpation device within the range between 10 µm and 20 µm may possibly be achieved. Further, the elasticity of the sample material 114 at the area of the surface area 112 may be evaluated at a depth of up to 3 mm below the surface of the sample material 114. In comparison, a known OCT-based optical palpation technique allows evaluating the elasticity of a sample material at a depth of 1-2 mm below the surface. Accordingly, the camera-based optical palpation device 100 and method 600 in accordance with embodiments of the present invention provide the advantage of an improved optical palpation technique with similar optical resolution and improved field of view within the sample material 114 as compared to currently known optical palpation techniques.

Further, the method 600 may comprise providing a motion detector (not shown) for detecting a position of the sensing layer 106 or of the device 100 relative to the sample material 114 when the device 100 is moved or scanned relative to the surface of the sample material 114. Thus, x and y coordinates for the sensing layer 106 or the device 100 across the surface of the sample material 114 can be obtained. The method 600 may then comprise moving the optical palpation device 100 across a plurality of surface areas 112 of the sample material 114 in a plane parallel to the surface of the sample material 114 and simultaneously performing steps 608 and 610 for each of the plurality of surface areas 112 across the sample material 114. Thus, the microprocessor 116 and graphical interface 118 may be used for forming a sequence of images of the sensing layer 106 as the device 100 is moved across the sample material 114 so that a change in the distribution of deformation across the sensing layer 106 can be tracked and observed as the device 100 is moved or scanned across the sample material 114. Alternatively, an image of the sensing layer 106 may be acquired for each of the plurality of surface areas 112 and the microprocessor 116 and graphical interface 118 may then be used to assemble the respective images as a function of the (x,y) coordinates of the sensing layer or device across the sample material to form one single image characteristic of the distribution of deformation across the sensing layer for an area of the sample material 114 including the plurality of studied surface areas 112. By detecting a movement or change in coordinates of the sensing layer 106 relative to the sample material 114 in the plane parallel to the surface of the sample material 114 and acquiring an image for each of the plurality of surface areas 112, the position of the sensing layer 106 or device 100 relative to the sample material 114 can be tracked and a global representation of the distribution of deformation and/or stress across the various scanned areas 112 of the sample material 114 can be obtained and observed in a single image. A stress map and/or strain map of the sample material 114 can thus be obtained. The pixel distribution of each of the plurality of optical images can then be analysed by digital image processing such that a quantitative measure of strain is obtained. The stress value can then be determined from a known stress-strain curve of the material comprising the sensing layer 106, and the elasticity of the sample material 114 can subsequently be quantitatively determined using the equation (1) defined above.

The processor 116 may further comprise a GPU and use a GPU algorithm to accelerate processing such that real-time images of the sensing layer 106 can be acquired as well as real-time images including the features indicative of a distribution of stress and/or deformation across the sensing layer caused by the applied pressure.

It is then further envisaged that the method 600 be implemented using AR devices or VR devices, such as a VR goggle, whereby the respective real-time images including features indicative of a distribution of stress and/or deformation across the sensing layer 106 can be overlapped with respective real-time images of the sensing layer 106 and projected onto a screen or embedded into the VR goggle such that the sense of touch can be enhanced.

Further, the camera-based optical palpation device such as device 100, or such as optical palpation device comprising optical system 400 or 500, may be incorporated within a surgical robot or video endoscope with the overlapped respective images projected onto a screen, which would allow providing tactile sensation during surgery.

Figure 7:
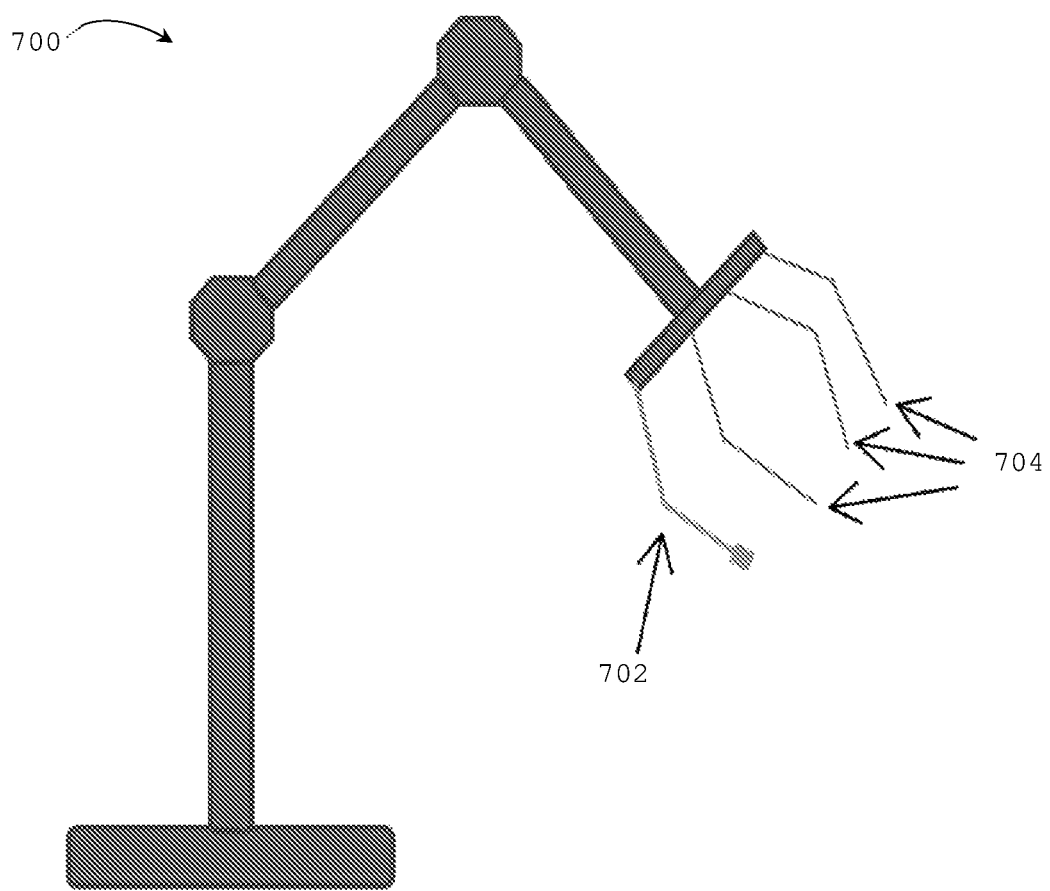
FIG. 7 shows a schematic representation of a robotic surgical device comprising an optical palpation device in accordance with an embodiment.

FIG. 7 shows an example of a robotic surgical device 700 incorporating a camera-based optical palpation device 702, which may correspond to optical palpation device 100 or optical palpation device comprising optical system 400 or 500. The optical palpation device 702 works as one of the surgical arms, allowing the robotic surgical device 700 to view the surgical site using the digital camera and to measure the mechanical property of a sample material (not shown) using the sensing layer 106 and the method 600. Further, information relating to the measured mechanical property of the sample material may be used to guide an operator of the robotic surgical device 700 through tactile sensing and/or imaging of the surgical site, i.e. sample material under investigation. The robotic surgical device 700 may further comprise other surgical arms or tolls 704.

Figure 8:
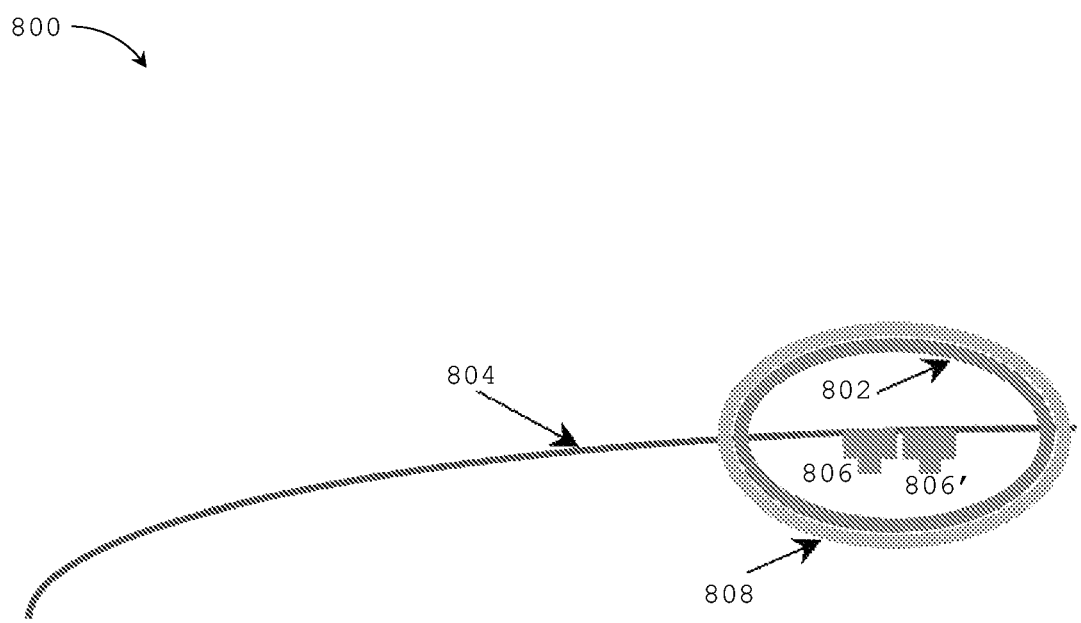
FIG. 8 shows a schematic representation of a balloon catheter comprising an optical palpation device in accordance with an embodiment.

FIG. 8 illustrates an embodiment wherein some components of a camera-based optical palpation device, which may correspond to optical palpation device 100 or optical palpation device comprising optical system 400 or 500, are positioned at or within a balloon catheter 800. The balloon catheter 800 comprises a balloon 802 and a catheter 804. As shown in FIG. 8, a camera 806 of the optical palpation device (or stereoscopic cameras 806, 806' for an optical palpation device comprising optical system 400 or 500) is positioned within the balloon 802 and a sensing layer 808 of the optical palpation device is positioned outside of the balloon 802, being attached to the outer surface of the balloon 802. To measure a mechanical property of a sample material (not shown), the balloon 802 is initially deflated and the catheter 804 is inserted into a target site of the sample material, e.g., an airway or vessel where the sample material is a biological tissue. When the catheter reaches the target site, the balloon is inflated such that the sensing layer 808 is compressed against the sample material. The camera or cameras of the optical palpation device can then be used to measure a mechanical property of the sample material, such as the elasticity, using the method 600. The optical palpation device and balloon catheter may further be arranged such that, simultaneously to measuring the mechanical property, the camera or cameras are used to acquire a photograph of the target site. In the particular example of the sample material being a biological tissue, the catheter may further incorporate other surgical tools, such as a blade or a fluid drainer, to work together with the optical palpation device. When the measurement and operation are done, the balloon 802 is deflated again, and the catheter can be withdrawn from the measurement site.

It will further be understood that, alternatively, it is also envisaged to have at least some or all components of the optical palpation device (such as optical palpation device 100 or comprising the optical system 400 or 500) positioned at or in a needle, probe or arthroscope, the needle probe or arthroscope having a window at which the sensing layer of the optical palpation device is positioned, such that a mechanical property of the sample material in which the needle, probe or arthroscope is in use positioned can be determined.

Figure 9:
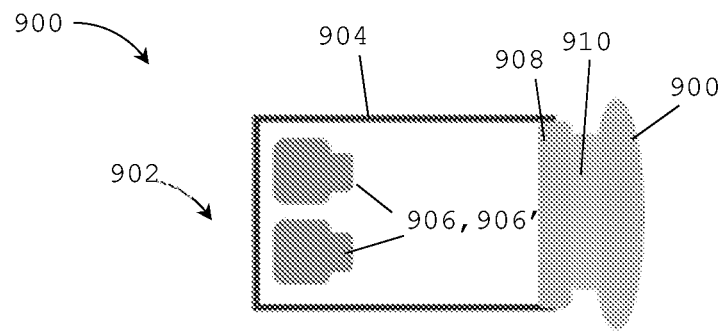
FIG. 9 shows a schematic representation illustrating a method for evaluating a mechanical property of a sample material performed in accordance with a further embodiment and using the optical palpation device of FIG. 1 or 4.
Figure 9:
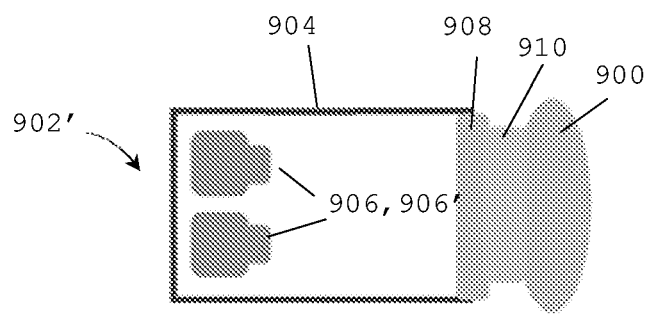
Figure 9:
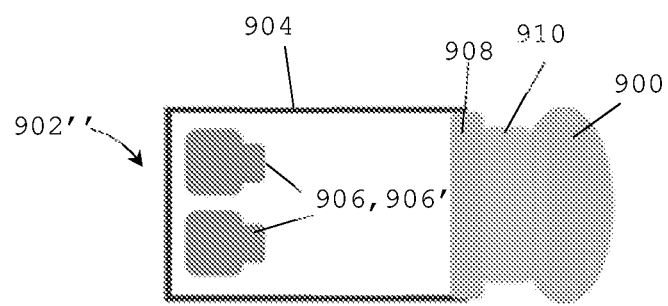

FIG. 9 illustrates a further application wherein the camera-based optical palpation device in accordance with embodiments of the disclosure is used to determine nonlinear mechanical properties of a sample material. FIG. 9 illustrates an embodiment wherein the method 600 is further used to measure nonlinear mechanical properties of a sample material 900 by applying varying different pressures, as illustrated at 902, 902', and 902". The optical palpation device 904 comprises in this particular embodiment a stereoscope with two cameras 906, 906', an imaging window 908 and a silicone sensing layer 910. It will be understood that the optical palpation device 904 may alternatively comprise a single camera 906. The optical palpation device 904 is used to compress the sensing layer 910 and the portion 912 of the sample material 900 continuously and the optical palpation device 904 with the sensing layer 910 is moved relative to the sample material 900 to apply the varying different pressures. The camera/cameras 906 may record continuous videos of the compressed layer, at a frame rate of for example 24 frames per second or higher, while the varying different pressures are applied and as the optical palpation device 904 moves relative to the sample material 900. A stress map of the sample material 900 can be obtained from the recorded video of the sensing layer 910, and a strain of the sample material 900 can be calculated from the moving speed of the optical palpation device 904 relative to the sample material 900, which can be measured using a gyroscope embedded in the optical palpation device 904. By determining the stress and strain of the sample material, the elasticity of the sample material 900 can be estimated. In particular, nonlinear mechanical properties of the sample material can be measured, such as nonlinear tangent modulus of the sample material, as continuous stress maps can be acquired at different strain points.

Figure 10:
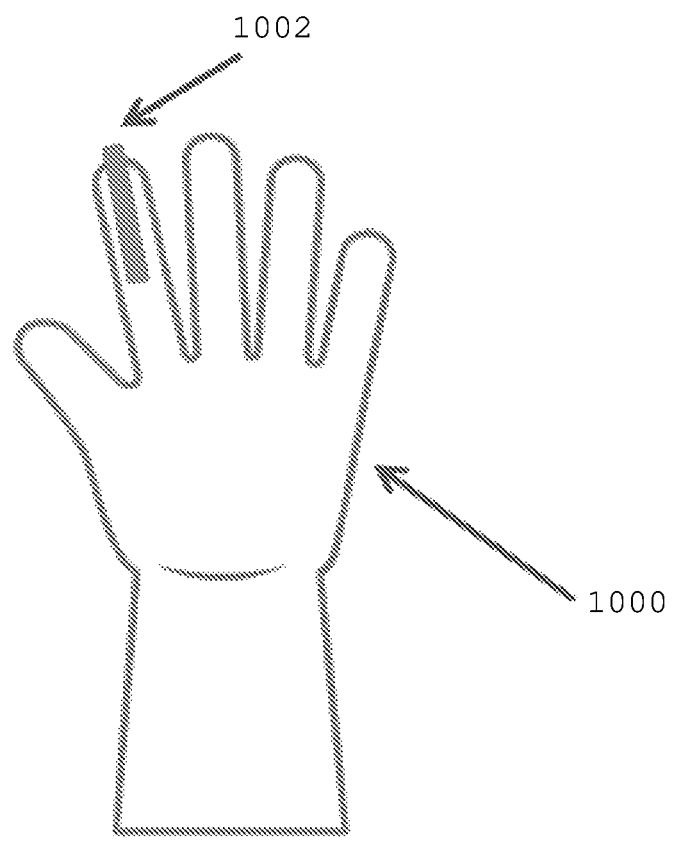
FIG. 10 shows a schematic representation of an optical palpation device incorporated in a glove in accordance with an embodiment.

FIG. 10 illustrates a further embodiment wherein a camera-based optical palpation device provided in accordance with embodiments of the present disclosure, such as optical palpation device 100 or the optical palpation device comprising the optical system 400 or 500, is incorporated in a surgical glove 1000. Camera-based optical palpation device 1002 is attached to a portion of the glove 1000, which is arranged such that a surgical operator can, in use, wear the glove and proceed to a measurement of stress of a target sample material and evaluation of the mechanical property of the target sample material, such as target biological tissue by performing steps 606 to 610 of method 600. A photography of the target sample material or tissue can also be obtained. In addition, the surgical operator wearing the glove may move the portion of the glove 1000 comprising the optical palpation device 1002 over the sample material for obtaining stress measurements and evaluating the mechanical property of the sample material across a predetermined area of the material. Once measurements are done, the camera-based optical palpation device 1002 can be detached from the surgical glove 1000 for the surgical operator to conduct other surgical operations. The compatibility of the camera-based optical palpation device to the surgical glove may present the advantage that time required for obtaining a measurement of the mechanical property of the sample material, such as tissue in this particular example, may be substantially reduced.

It will be appreciated that although the present embodiment has been described in relation to a surgical glove, the optical palpation device may be incorporated in other types of gloves, which may be used in relation to other applications wherein the sample material may not be limited to a biological tissue.

Figure 11:
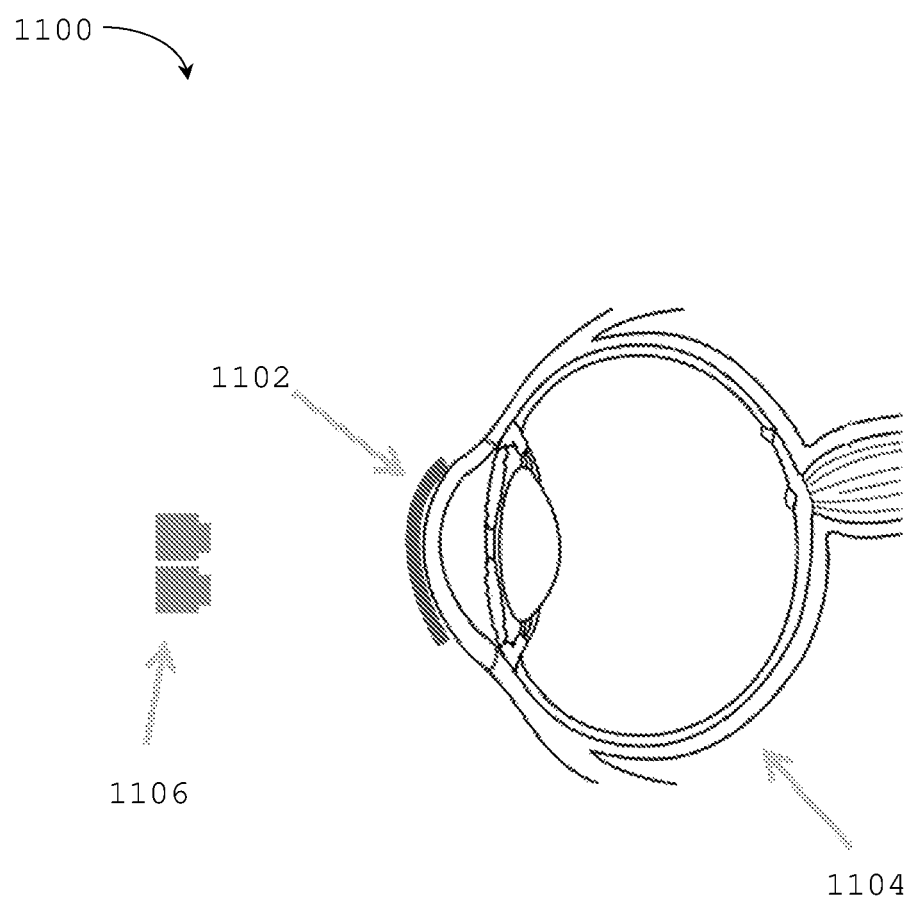
FIG. 11 shows a schematic representation of an optical palpation device incorporated into a contact lens system in accordance with another embodiment.

FIG. 11 illustrates another embodiment wherein a camera-based optical palpation device provided in accordance with embodiments of the present disclosure, such as optical palpation device 100 or the optical palpation device comprising the optical system 400 or 500, is incorporated in a contact lens system 1100. In this embodiment, the sensing layer of the optical palpation device is provided in the form of a lens 1102 arranged for positioning at the surface of an eye 1104 of a patient. As the eye pressure changes, the thickness of the sensing layer 1104 changes accordingly. Cameras 1106 of the optical palpation device are arranged such that the change in thickness of the sensing layer 1104 can be measured, whereby variations in the eye pressure and/or the stiffness of the eye can be determined.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. An optical palpation device for evaluating a mechanical property of a sample material, the device comprising:
    a body having a sensing portion;
    a sensing layer positioned at the sensing portion of the body and having a sensing surface positioned for direct or indirect contact with a surface area of the sample material, the sensing layer being deformable and having an optically detectable marker or pattern;
    an optical system capable of providing information that can be used to determine a movement of the marker or pattern relative to the optical system and upon deformation of the sensing layer, the information being provided for a plane orthogonal to a direction of propagation of light;
    wherein the optical palpation device is arranged such that, when the sensing surface of the sensing layer is in direct or indirect contact with the surface area of the sample material and a pressure is applied across both the sensing layer and at least a portion of the surface area of the sample material, the sensing layer is deformed and information concerning the mechanical property of the sample material can be provided by measuring a change in position of the marker or pattern relative to the optical system;
    wherein the optical system comprises a stereoscopic camera; and
    wherein the marker or pattern is at least one of:
        (i) intrinsic to the sensing layer; and
        (ii) illuminated by a light source projecting a light.

2. The optical palpation device of claim 1 wherein the optical system comprises at least two spaced apart light detector components positioned to detect light reflected or transmitted from the marker or pattern.

3. The optical palpation device of claim 1 wherein the optical system comprises an array of optical elements for detecting light transmitted through the sensing layer, and that are positioned such that a depth position of the marker or pattern can be determined.

4. The optical palpation device of claim 1 wherein the optical palpation device is a hand-held device.

5. The optical palpation device of claim 1 wherein the markers comprise fluorescent particles or photoluminescent particles.

6. The optical palpation device of claim 1 wherein the device is arranged such that photographs and mechanical properties of the sample material can be acquired simultaneously.

7. The optical palpation device of claim 1 wherein the markers comprise transparent particles.

8. The optical palpation device of claim 1 wherein the mechanical property is elasticity and the detected light is indicative of a distribution of stress and/or deformation across the sensing layer in response to the applied pressure, the distribution of stress and/or deformation being associated with the mechanical property of the sample material.

9. The optical palpation device of claim 1 wherein the sample material is a biological tissue or a biological material.

10. The optical palpation device of claim 1 comprising a motion detector for detecting a position or motion of the sensing layer or the device relative to the sample material when the device is moved or scanned relative to a surface of the sample material.

11. An optical palpation device for evaluating a mechanical property of a sample material, the device comprising:
    a body having a sensing portion;
    a sensing layer positioned at the sensing portion of the body and having a sensing surface positioned for direct or indirect contact with a surface area of the sample material, the sensing layer being deformable and having a predetermined deformation-dependent optical property; and
    a light detector positioned to detect light transmitted through at least a portion of the sensing layer;

wherein the optical palpation device is arranged such that, when the sensing surface of the sensing layer is in direct or indirect contact with the surface area of the sample material and a pressure is applied through both the sensing layer and at least a portion of the surface area of the sample material, the sensing layer is deformed and because of the predetermined deformation-dependent optical property of the sensing layer the mechanical property of the sample material is measurable by detecting the light that transmitted through at least a portion of the sensing layer;

wherein the sensing layer is compressible such that a volume of the sensing layer changes upon axial loading;

wherein the predetermined deformation-dependent optical property is a compression dependent optical property; and wherein the sensing layer is configured to become more transparent upon application of a compressive load.

12. The optical palpation device of claim 11 wherein the predetermined deformation-dependent optical property of the sensing layer is compression-dependent transmissivity, light polarisation, light absorption, or light scattering.

13. The optical palpation device of claim 11 wherein the optical palpation device is a hand-held device or a video endoscope.

14. The optical palpation device of claim 11 wherein the mechanical property is elasticity and the detected light is indicative of a distribution of stress and/or deformation across the sensing layer in response to the applied pressure, the distribution of stress and/or deformation being associated with the mechanical property of the sample material.

15. The optical palpation device of claim 11 wherein the light detector comprises a stereoscopic camera.

16. A system for evaluating a mechanical property of a sample material, the system comprising:
the optical palpation device in accordance with claim 11; and
a processor coupled to the optical palpation device and configured to receive a signal indicative of information associated with the light detected by the light detector;
wherein the information can be used to obtain a measure of the mechanical property of the sample material.

17. A method for evaluating a mechanical property of a sample material, the method comprising:
providing the sample material;
providing a system in accordance with the claim 16;
the method further comprising:
positioning the sensing layer relative to the sample material such that the sensing surface is in direct or indirect contact with a surface area of the sample material;
applying a pressure through both the sensing layer and at least a portion of the surface area of the sample material; and
detecting light transmitted or reflected from at least a portion of the sensing layer.

18. The method of claim 17 comprising:
providing a motion detector for detecting a position of the sensing layer or the device relative to the sample material when the device is moved or scanned relative to a surface of the sample material;
moving the optical palpation device across a plurality of surface areas of the sample material while (i) applying a pressure through both the sensing layer and at least a portion of a respective surface area of the sample material such that the sensing layer is compressed and (ii) either simultaneously detecting light transmitted through, or reflected from, at least a portion of the sensing layer for each of the plurality of surfaces areas of the sample material, or sequentially detecting light during movement of the device across the sample material; and
detecting a movement or change in coordinates of the sensing layer or the device relative to the sample material.

19. The optical palpation device of claim 11 wherein the sensing layer is movable between:
an uncompressed state in which no compressive load is applied; and
a compressed state in which the compressive load is applied and the sensing layer is more transparent than when in the uncompressed state.

20. The optical palpation device of claim 11 wherein the sensing layer:
comprises air cavities; and
is configured to be compressed without expanding in a lateral direction.

* * * * *